(12) United States Patent
Hamada et al.

(10) Patent No.: US 8,278,333 B2
(45) Date of Patent: Oct. 2, 2012

(54) CRYSTALS OF BENZOXADIAZOLE DERIVATIVE

(75) Inventors: Noritaka Hamada, Tokyo (JP); Ryo Mizoguchi, Tokyo (JP); Kuniyuki Sano, Tokyo (JP); Takaaki Sakaida, Tokyo (JP); Yuji Awamura, Tokyo (JP); Yu Iwakawa, Tokyo (JP); Takahiko Tobe, Tokyo (JP); Takashi Sugane, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 534 days.

(21) Appl. No.: 12/307,843

(22) PCT Filed: Jul. 13, 2007

(86) PCT No.: PCT/JP2007/063960
§ 371 (c)(1),
(2), (4) Date: Jan. 7, 2009

(87) PCT Pub. No.: WO2008/007766
PCT Pub. Date: Jan. 17, 2008

(65) Prior Publication Data
US 2009/0203741 A1    Aug. 13, 2009

(30) Foreign Application Priority Data
Jul. 14, 2006 (JP) ................... 2006-193855

(51) Int. Cl.
*A61K 31/4439* (2006.01)
*C07D 413/14* (2006.01)

(52) U.S. Cl. .................. 514/338; 546/269.1

(58) Field of Classification Search .............. 546/269.1; 514/338
See application file for complete search history.

(56) References Cited

U.S. PATENT DOCUMENTS

| 5,614,651 | A | 3/1997 | Ohtsuki et al. | |
|---|---|---|---|---|
| 5,648,507 | A | 7/1997 | Ohtsuki et al. | |
| 6,627,646 | B2 * | 9/2003 | Bakale et al. | 514/322 |
| 7,034,047 | B2 * | 4/2006 | Tobe et al. | 514/383 |
| 7,084,164 | B2 * | 8/2006 | Tobe et al. | 514/383 |
| 2003/0216385 | A1 | 11/2003 | Tobe et al. | |

FOREIGN PATENT DOCUMENTS

| JP | 07-41495 A | 2/1995 |
|---|---|---|
| JP | 2004-175788 A | 6/2004 |
| WO | 01/87855 A1 | 11/2001 |

OTHER PUBLICATIONS

Chemical & Engineering News, Feb. 2003, 32-35.*
Brittain ed.,"Polymorphism in Pharmaceutical Solids.," NY:Marcel Dekker, Inc., 1999, 1-2, 183-226, 235-238.*
Concise Encyclopedia Chemistry, NY: Walter de Gruyter, 1993, 872-873.*
Rowland & Tozer, "Clinical Pharmacokinetics, etc.," 1995, p. 123.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Silverman, The Organic Chemistry of Drug Design and Drug Action, NY: Academic Press, 1993, 72-76.*
Ulicky. Comprehensive Dictionary of Physical Chemistry, NY: Prentice Hall, 1992, p. 21.*
Doelker, english translation of Ann. Pharm. Fr., 2002, 60: 161-176, pp. 1-39.*
Doelker, english translation of S.T.P, Pratiques (1999), 9(5), 399-409, pp. 1033.*
Otuska et al., "Effect of Polymorphic, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*
Bernstein et al., "Polymorphism in Molecular Crystals", Oxford: Clarendon Press, 2002, pp. 117, 118, 272 and 273.*
Davidovich et al., "Detection of Polymorphism, etc.," American Pharmaceutical Review, IN: Russell Pub., 2004, 7(1), pp. 10, 12, 14, 16 and 100.*

* cited by examiner

*Primary Examiner* — Patricia Morris
(74) *Attorney, Agent, or Firm* — Sughrue Mion, PLLC

(57) ABSTRACT

Object
Provided are β-form crystal, γ-form crystal, and α-form crystal of a benzoxadiazole derivative, wherein a uniform crystal having sufficient qualities can be obtained with high reproducibility, and they can be anytime supplied as crystals of drug substance for use in producing pharmaceuticals, are particularly suitable for mass synthesis in industrial production, hardly exhibit hygroscopicity and have particularly excellent photo-resistance.
Means for Resolution
A solving means includes β-form crystal of 4-[3-isopropyl-5-(6-phenyl-3-pyridyl)-4H-1,2,4-triazol-4-yl]-2,1,3-benzoxadiazole, which shows an endothermic peak at 145 to 150° C. according to a differential scanning calorimeter analysis (DSC analysis) and shows X-ray powder diffraction peaks at 9.8, 11.1, 12.8, 13.3, 17.1, 20.2, 21.2 and 22.3 in 2θ(°), and the like.

4 Claims, 12 Drawing Sheets

CRYSTALS OF BENZOXADIAZOLE DERIVATIVE

TECHNICAL FIELD

The present invention relates to new crystals of 4-[3-isopropyl-5-(6-phenyl-3-pyridyl)-4H-1,2,4-triazol-4-yl]-2,1,3-benzoxadiazole (hereinafter, it may be simply referred to as "compound A"). More specifically, the present invention relates to novel β-form crystal, γ-form crystal, and α-form crystal of the compound A, wherein a uniform crystal having sufficient qualities can be obtained with high reproducibility, and also they can be anytime supplied as crystals of drug substance for use in producing pharmaceuticals, are suitable in mass synthesis for industrial production, hardly exhibit hygroscopicity and have excellent photo-resistance, also relates to a pharmaceutical composition comprising the same as an active ingredient and useful as a glycine transporter inhibitor, particularly as a therapeutic agent for dementia or a therapeutic agent for schizophrenia.

BACKGROUND ART

The inventors of the present invention have reported that 4-[3-isopropyl-5-(6-phenyl-3-pyridyl)-4H-1,2,4-triazol-4-yl]-2,1,3-benzoxadiazole (compound A) represented by the following chemical formula is useful as a pharmaceutical agent, in particular, as an inhibitor of glycine transporter activity, for example, as a therapeutic agent for dementia or schizophrenia (see Example 2, Patent Document 1).

In Example 2 of Patent Document 1, 4-[3-isopropyl-5-(6-phenylpyridine-3-yl)-4H-1,2,4-triazol-4-yl]-2,1,3-benzoxadiazole is given as compound A, and this is an identical compound to 4-[3-isopropyl-5-(6-phenyl-3-pyridyl)-4H-1,2,4-triazol-4-yl]-2,1,3-benzoxadiazole, and both nomenclatures refer to the compound shown below.

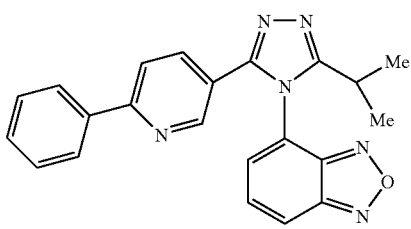

[Chem. 1]

Patent Document 1: Pamphlet of International Publication No. 2001/87855

DISCLOSURE OF THE INVENTION

Problems to be Solved by the Invention

A white crystal of the compound A, having a melting point of 107 to 108° C. is disclosed in Example 2 of Patent Document 1, but other crystal forms are not disclosed at all. The inventors of the present invention have studied extensively on the crystal polymorphism of the compound A, and have confirmed a total of 4 forms of crystal forms of the compound A, which are α-form (alpha), β-form (beta), γ-form (gamma), and δ-form (delta). Furthermore, the white crystal of the compound A having a melting point of 107 to 108° C. disclosed in Example 2 of Patent Document 1 mentioned above is verified as the δ-form crystal.

It was found that although the δ-form crystal of the compound A can be obtained in a small scale as mentioned in Example 2 of Pamphlet of International Publication No. 2001/87855, it is technically difficult to obtain the target polymorph as a uniform crystal with excellent reproducibility in the process of producing drug substances in performing a mass synthesis. In addition, it was realized that it is technically difficult to anytime supply the bulk drug crystals having sufficient qualities, and a considerably high cost is required for the stable supply. Furthermore, it was also found that the δ-form crystal exhibits hygroscopicity, and is unstable under the light exposure condition. Consequently, it was virtually impossible to use the δ-form crystal of the compound A as a drug substance in the production of pharmaceuticals.

The present invention is made to solve the aforementioned problems, and specifically, an object of which is to provide β-form crystal, γ-form crystal, and α-form crystal of the compound A, wherein a uniform crystal having sufficient qualities can be obtained with high reproducibility, and they can be anytime supplied as crystals of drug substance for use in producing pharmaceuticals, are suitable in mass synthesis for industrial production, hardly exhibit hygroscopicity and have excellent photo-resistance thereby being excellent in preservation.

Means for Solving the Problems

In order to accomplish the aforementioned object, the inventors of the present invention have studied extensively on the crystal polymorphisms of the compound A, and as a result, they found that, in the case of β-form crystal, γ-form crystal, and α-form crystal of the compound A, a uniform crystal having sufficient qualities can be obtained with high reproducibility, anytime supply of them as crystals of drug substance for use in producing pharmaceuticals is possible, hygroscopicity can be avoided, and excellent photo-resistance is provided. Thus, they have completed the present invention. That is, in order to accomplish the above objects, the present invention provides, as shown below, novel β-form crystal, γ-form crystal and α-form crystal of the compound A, as well as a pharmaceutical composition comprising the same as an active ingredient and useful as a glycine transporter inhibitor, particularly as a therapeutic agent for dementia or a therapeutic agent for schizophrenia. Preferred embodiments of the present invention are listed below.

[1] A β-form crystal of 4-[3-isopropyl-5-(6-phenyl-3-pyridyl)-4H-1,2,4-triazol-4-yl]-2,1,3-benzoxadiazole.

[2] A β-form crystal of 4-[3-isopropyl-5-(6-phenyl-3-pyridyl)-4H-1,2,4-triazol-4-yl]-2,1,3-benzoxadiazole, which shows an endothermic peak at 145 to 150° C. according to a differential scanning calorimeter analysis (DSC analysis).

[3] A β-form crystal of 4-[3-isopropyl-5-(6-phenyl-3-pyridyl)-4H-1,2,4-triazol-4-yl]-2,1,3-benzoxadiazole, which shows X-ray powder diffraction peaks at 9.8, 11.1, 12.8, 13.3, 17.1, 20.2, 21.2 and 22.3 in 2θ(°).

[4] A β-form crystal of 4-[3-isopropyl-5-(6-phenyl-3-pyridyl)-4H-1,2,4-triazol-4-yl]-2,1,3-benzoxadiazole, which shows an endothermic peak at 145 to 150° C. according to a differential scanning calorimeter analysis (DSC analysis) and shows X-ray powder diffraction peaks at 9.8, 11.1, 12.8, 13.3, 17.1, 20.2, 21.2 and 22.3 in 2θ(°).

[5] A pharmaceutical composition which comprises the β-form crystal of any one of above [1] to [4] as an active ingredient.

[6] The pharmaceutical composition according to above [5], which further comprises a pharmaceutically acceptable excipient.

[7] The pharmaceutical composition according to above [5], which is a glycine transporter inhibitor.

[8] The pharmaceutical composition according to above [5], which is a therapeutic agent for dementia or a therapeutic agent for schizophrenia.

[9] A γ-form crystal of 4-[3-isopropyl-5-(6-phenyl-3-pyridyl)-4H-1,2,4-triazol-4-yl]-2,1,3-benzoxadiazole.

[10] A γ-form crystal of 4-[3-isopropyl-5-(6-phenyl-3-pyridyl)-4H-1,2,4-triazol-4-yl]-2,1,3-benzoxadiazole, which shows an endothermic peak at 149 to 154° C. according to a differential scanning calorimeter analysis (DSC analysis).

[11] A γ-form crystal of 4-[3-isopropyl-5-(6-phenyl-3-pyridyl)-4H-1,2,4-triazol-4-yl]-2,1,3-benzoxadiazole, which shows X-ray powder diffraction peaks at 8.3 16.7, 18.9, 21.4, 22.2, 23.0, 24.6, 24.9 and 25.6 in 2θ(°).

[12] A γ-form crystal of 4-[3-isopropyl-5-(6-phenyl-3-pyridyl)-4H-1,2,4-triazol-4-yl]-2,1,3-benzoxadiazole, which shows an endothermic peak at 149 to 154° C. according to a differential scanning calorimeter analysis (DSC analysis) and shows X-ray powder diffraction peaks at 8.3 16.7, 18.9, 21.4, 22.2, 23.0, 24.6, 24.9 and 25.6 in 2θ(°).

[13] A pharmaceutical composition which comprises the γ-form crystal of any one of above [9] to [12] as an active ingredient.

[14] The pharmaceutical composition according to above [13], which further comprises a pharmaceutically acceptable excipient.

[15] The pharmaceutical composition according to above [13], which is a glycine transporter inhibitor.

[16] The pharmaceutical composition according to above [13], which is a therapeutic agent for dementia or a therapeutic agent for schizophrenia.

[17] An α-form crystal of 4-[3-isopropyl-5-(6-phenyl-3-pyridyl)-4H-1,2,4-triazol-4-yl]-2,1,3-benzoxadiazole.

[18] An α-form crystal of 4-[3-isopropyl-5-(6-phenyl-3-pyridyl)-4H-1,2,4-triazol-4-yl]-2,1,3-benzoxadiazole, which shows an endothermic peak at 168 to 173° C. according to a differential scanning calorimeter analysis (DSC analysis).

[19] An α-form crystal of 4-[3-isopropyl-5-(6-phenyl-3-pyridyl)-4H-1,2,4-triazol-4-yl]-2,1,3-benzoxadiazole, which shows X-ray powder diffraction peaks at 9.1, 10.4, 13.0, 13.7, 19.3, 20.8, 22.9, 25.2 and 25.9 in 2θ(°).

[20] An α-form crystal of 4-[3-isopropyl-5-(6-phenyl-3-pyridyl)-4H-1,2,4-triazol-4-yl]-2,1,3-benzoxadiazole, which shows an endothermic peak at 168 to 173° C. according to a differential scanning calorimeter analysis (DSC analysis) and shows X-ray powder diffraction peaks at 9.1, 10.4, 13.0, 13.7, 19.3, 20.8, 22.9, 25.2 and 25.9 in 2θ(°).

[21] A pharmaceutical composition which comprises the α-form crystal of any one of above [17] to [20] as an active ingredient.

[22] The pharmaceutical composition according to above [21], which further comprises a pharmaceutically acceptable excipient.

[23] The pharmaceutical composition according to above [21], which is a glycine transporter inhibitor.

[24] The pharmaceutical composition according to above [21], which is a therapeutic agent for dementia or a therapeutic agent for schizophrenia.

Effect of the Invention

According to the present invention, there are provided novel β-form crystal, γ-form crystal, and α-form crystal of the compound A, wherein a uniform crystal having sufficient qualities can be obtained with high reproducibility, anytime supply of them as crystals of drug substance for use in producing pharmaceuticals is possible, hygroscopicity can be avoided, and excellent photo-resistance is provided; as well as a pharmaceutical composition comprising the same as an active ingredient and particularly useful as a therapeutic agent for dementia or a therapeutic agent for schizophrenia.

BEST MODE FOR CARRYING OUT THE INVENTION

Hereinafter, preferred embodiments for carrying out the present invention will be described in detail.

The β-form crystal, the γ-form crystal and the α-form crystal of 4-[3-isopropyl-5-(6-phenyl-3-pyridyl)-4H-1,2,4-triazol-4-yl]-2,1,3-benzoxadiazole (hereinafter, these may be referred to as "β-form crystal of the present invention", "γ-form crystal of the present invention" and "α-form crystal of the present invention", respectively) are different from the known δ-form crystal in that a uniform crystal having sufficient qualities can be obtained with excellent reproducibility. Furthermore, stable supply of them as crystals of drug substance for use in producing pharmaceuticals is possible, hygroscopicity can be avoided, and particularly excellent photo-resistance is provided. Each crystal form can be identified particularly by differential scanning calorimeter analysis (DSC analysis) and X-ray powder diffraction.

Specifically, the β-form crystal of the present invention shows an endothermic peak at 145 to 150° C. according to a differential scanning calorimeter analysis (DSC analysis) and/or shows X-ray powder diffraction peaks near at 9.8, 11.1, 12.8, 13.3, 17.1, 20.2, 21.2 and 22.3 in 2θ(°).

In addition, the γ-form crystal of the present invention shows an endothermic peak at 149 to 154° C. according to a differential scanning calorimeter analysis (DSC analysis) and/or shows X-ray powder diffraction peaks near at 8.3, 16.7, 18.9, 21.4, 22.2, 23.0, 24.6, 24.9 and 25.6 in 2θ(°).

Furthermore, the α-form crystal of the present invention shows an endothermic peak at 168 to 173° C. according to a differential scanning calorimeter analysis (DSC analysis) and/or shows X-ray powder diffraction peaks near at 9.1, 10.4, 13.0, 13.7, 19.3, 20.8, 22.9, 25.2 and 25.9 in 2θ(°).

On the other hand, the known δ-form crystal shows an endothermic peak at around 100° C. according to a differential scanning calorimeter analysis (DSC analysis) and/or shows X-ray powder diffraction peaks near at 6.6, 8.0, 12.7, 15.3, 18.0, 20.0 and 23.0 in 2θ(°).

In Table 1, the diffraction angle (2θ(°)) and the relative intensity of the β-form crystal, the γ-form crystal and the α-form crystal of the present invention as well as the known δ-form crystal, in the pattern of the X-ray powder diffraction are listed. The 4 forms of crystals are distinguished one from others by the diffraction angles and the relative intensities.

However, with regard to the X-ray powder diffraction, since crystal lattice spaces or overall patterns are important in confirming the identity of the crystals according to the nature of the data, and the relative intensities somewhat vary depending on the direction of a crystal growth, a size of particles, and the measurement conditions, the relative intensities should not be interpreted strictly.

TABLE 1

| β-form Crystal (crystal of present invention) | | γ-form Crystal (crystal of present invention) | | α-form Crystal (crystal of present invention) | | δ-form Crystal (known crystal) | |
|---|---|---|---|---|---|---|---|
| Diffraction Angle | Relative Intensity | Diffraction Angle | Relative Intensity | Diffraction Angle | Relative Intensity | Diffraction Angle | Relative Intensity |
| 9.8 | Medium | 8.3 | Strong | 9.1 | Medium | 6.6 | Strong |
| 11.1 | Weak | 16.7 | Weak | 10.4 | Weak | 8.0 | Medium |
| 12.8 | Medium | 18.9 | Weak | 13.0 | Weak | 12.7 | rather Strong |
| 13.3 | Medium | 21.4 | Weak | 13.7 | Strong | 15.3 | Medium |
| 17.1 | rather Strong | 22.2 | Weak | 19.3 | Weak | 18.0 | Medium |
| 20.2 | rather Strong | 23.0 | Weak | 20.8 | Medium | 20.0 | Medium |
| 21.2 | Strong | 24.6 | Weak | 22.9 | Strong | 23.0 | rather strong |
| 22.3 | rather Strong | 24.9 | Weak | 25.2 | Weak | | |
| | | 25.6 | Weak | 25.9 | Weak | | |

The "X-ray Powder Diffraction", the "Differential Scanning Calorimeter Analysis (DSC Analysis)", "Hygroscopicity" and "Photo stability" were measured under the conditions below, respectively.

(X-ray Powder Diffraction)

The measurement was carried out using "MAC Science MXP18TAHF22", under the conditions of tube: Cu, tube current: 40 mA, tube voltage: 40 or 200 kV, sampling width: 0.020°, scanning speed: 3°/min, wavelength: 1.54056 Å, and diffraction measurement range (2θ): 3 or 5 to 40°.

The measurement was carried out using "Bruker D8 with GADDS", under the conditions of tube: Cu, tube current: 40 mA, tube voltage: 40 kV, wavelength: 1.54056 Å, θ1: 5°, θ2: 10°, collimator: 0.3 mmφ, detector distance: 25 cm, measurement time: 180 s, and integration range: 5 to 26°.

(Differential Scanning Calorimeter Analysis (DSC Analysis))

The measurement was carried out using "TA Instrument TA5000" or "TA Instrument Q-1000", under the conditions of room temperature to 300° C. (10 or 30° C./min), $N_2$ (50 ml/min), and an aluminum sample pan.

(Hygroscopicity)

The measurement was carried out using "DVS" or "SGA-100", under the conditions of temperature: 25° C., measurement range: 5 to 95% relative humidity, and measurement interval: 5% relative humidity.

(Photo Stability)

The amount of impurity was measured through HPLC using a preserved sample, under 1.2 million lux-hours (temperature: 25° C.) of integrated luminance, using a light stability testing device LTL-200D3J-15.

(Preparation Method)

The β-form crystal of the present invention can be prepared from the compound A disclosed in Example 2 of Patent Document 1, for example, by the method below.

The compound A, synthesized as in Example 2 of Pamphlet of International Publication No. 2001/87855, is heated and stirred in 8 to 61-fold volume of ethanol-water mixed solution (2:1 to 1:2) or toluene until fully dissolved. This solution is filtered under heating, washed with an ethanol-water mixed solution or toluene mixed solvent, and then cooled. The crystal is precipitated followed by stirring at 20 to 30° C. for 1 to 2 hour(s), and further stirring at 0 to 5° C. for 8 to 24 hours. The precipitated crystal is filtered, washed with a mixed solvent of ethanol and water, and then dried under reduced pressure to obtain β-form crystal of 4-[3-isopropyl-5-(6-phenyl-3-pyridyl)-4H-1,2,4-triazol-4-yl]-2,1,3-benzoxadiazole.

In addition, the γ-form crystal of the present invention can be prepared, for example, by the method below.

A crude product of the compound A, synthesized as in Example 2 of Pamphlet of International Publication No. 2001/87855, is purified by silica gel column chromatography, and a hexane-ethyl acetate mixed solution mixed in an adequate ratio was added to the obtained residue, followed by stirring at 20 to 30° C. for 1 to 2 hour(s). The precipitated crystal is filtered, washed with hexane-ethyl acetate mixed solution, and then dried under reduced pressure to obtain γ-form crystal of 4-[3-isopropyl-5-(6-phenyl-3-pyridyl)-4H-1,2,4-triazol-4-yl]-2,1,3-benzoxadiazole.

Moreover, the α-form crystal of the present invention can be prepared, for example, by the method below.

The compound A, obtained as in Example 2 of Patent Document 1, is added with ethanol:water=1:2 to 1:4 and heated and stirred until fully dissolved. The mixture is left to cool down to room temperature, the precipitated crystal is filtered, washed with ethanol:water=1:3 to 1:5, and then dried under reduced pressure to obtain the α-form crystal of 4-[3-isopropyl-5-(6-phenyl-3-pyridyl)-4H-1,2,4-triazol-4-yl]-2,1,3-benzoxadiazole.

The pharmaceutical compositions of the present invention contain the above-mentioned β-form crystal, γ-form crystal, α-form crystal or their arbitrary combinations, as an active ingredient, as well as contain pharmaceutically acceptable excipients, and are useful as a glycine transporter inhibitor. In addition, the compositions are particularly useful as a therapeutic agent for dementia or a therapeutic agent for schizophrenia.

The pharmaceutical compositions which contain 1 or 2 or more forms of the crystals of the present invention as active ingredients can be manufactured in the form of tablets, powders, fine granules, granules, capsules, pills, liquid medicines, injection medicines, suppositories, ointments, or adhesives by employing typically-used carriers, fillers or other additives of drug products, and can be administered orally or parenterally.

The clinical dosages of the crystals of the present invention for humans are determined appropriately in consideration of a patient's symptoms, body weight, age and gender, but for an adult, the dosage is typically 0.1 to 500 mg per day per oral, or 0.01 to 100 mg per day parenterally, and is administered singularly or in divisions. The dosage varies depending on numerous conditions, thus in some cases a smaller amount than the above-mentioned dosage amount may be sufficient.

As solid compositions of the present invention for oral administration, tablets, powders, granules and the like are employed. For these solid compositions, one or more active materials are mixed with at least one inert diluent, for example, lactose, mannitol, glucose, hydroxypropyl cellulose, fine crystal cellulose, starch, polyvinyl pyrolidone, or magnesium aluminate metasilicate. By common procedures, the composition may contain additives other than inert diluents, for example, lubricants such as magnesium stearinate, disintegrants such as calcium cellulose glycolate, stabilizers such as lactose, or solubilizers or solubilizing agents such as glutamic acid or aspartic acid. The tablets or pills may be sugar-coated, or coated with films of gastrosoluble or enterosoluble materials, such as sucrose, gelatin, hydroxypropyl cellulose, hydroxypropylmethyl cellulose phthalate and the like as necessary.

As liquid compositions for oral administration, pharmaceutically acceptable emulsions, solutions, suspensions, syrups, elixirs and the like are included, as well as typically-used inert diluents, for example, purified water or ethyl alcohol. These compositions may contain supplements, such as solubilizers, solubilizing agents, moisturizers, and suspensions, sweeteners, fragrancers, air-fresheners, and preservatives.

As injection medicines for parenteral administration, sterile aqueous or non-aqueous solutions, suspensions and emulsions are included. As diluents for aqueous solutions and suspensions, for example, distilled water for injection and physiological saline are included. As diluents for non-aqueous solutions and suspensions, for example, plant oils such as propylene glycol, polyethylene glycol and olive oils, alcohols such as ethyl alcohol, and Polysorbate 80 (trade name) are included.

These compositions may also contain additives such as tonics, preservatives, moisturizers, emulsifiers, dispersers, stabilizers (for example, lactose), solubilizers or solubilizing agents. These are sterilized by, for example, filtration through a bacteria-containing filter, bactericidal compounds, or irradiation. Furthermore, these compositions can also be manufactured as sterile solid compositions and dissolved in sterile water or sterile solvents for injection before use.

EXAMPLES

Hereinbelow, the present invention is explained in detail with reference to Examples, but the present invention is not limited by Examples in any ways. In addition, the δ-from crystal of the compound A will be explained in Comparative Example.

Example 1

β-form Crystal of 4-[3-isopropyl-5-(6-phenyl-3-pyridyl)-4H-1,2,4-triazol-4-yl]-2,1,3-benzoxadiazole The compound A (27.96 kg), synthesized as in Example 2 of Pamphlet of International Publication No. 2001/87855 (Patent Document 1), was heated and stirred in ethanol (154 L) and water (77 L) until fully dissolved. The solution was filtered under heating, washed with a mixture of ethanol (14 L) and water (7 L), and then cooled down. The crystal was precipitated, followed by stirring at 20° C. for 1.5 hours, and further stirring at 0° C. for overnight. The precipitated crystal was filtered, washed with a mixture of ethanol and water, and then dried at 60° C. under reduced pressure to obtain the β-form crystal (25.64 kg) of 4-[3-isopropyl-5-(6-phenyl-3-pyridyl)-4H-1,2,4-triazol-4-yl]-2,1,3-benzoxadiazole.

FIG. 1 shows the differential scanning calorimeter analysis curve (DSC analysis curve) of the β-form crystal, and FIG. 2 shows the X-ray powder diffraction pattern of the β-form crystal.

Example 2

γ-form Crystal of 4-[3-isopropyl-5-(6-phenyl-3-pyridyl)-1,2,4-triazol-4-yl]-2,1,3-benzoxadiazole A crude substance (6.22 g) of 4-[3-isopropyl-5-(6-phenyl-3-pyridyl)-4H-1,2,4-triazol-4-yl]-2,1,3-benzoxadiazole, obtained as in Example 2 of Patent Document 1, was purified by silica gel column chromatography (developing solvent: chloroform-chloroform/methanol=100/1 to 50/1 to 30/1). The obtained residue was added with hexane:ethyl acetate=15:1 (50 mL), followed by stirring at room temperature for 1 hour, the precipitated crystal was filtered, washed with hexane:ethyl acetate=50:1, and then dried at 40° C. under reduced pressure to obtain the γ-form crystal (5.31 g) mentioned above.

FIG. 3 shows the differential scanning calorimeter analysis curve (DSC analysis curve) of the γ-form crystal, and FIG. 4 shows the X-ray powder diffraction pattern of the γ-form crystal.

Example 3

α-form Crystal of 4-[3-isopropyl-5-(6-phenyl-3-pyridyl)-4H-1,2,4-triazol-4-yl]-2,1,3-benzoxadiazole 4-[3-isopropyl-5-(6-phenyl-3-pyridyl)-4H-1,2,4-triazol-4-yl]-2,1,3-benzoxadiazole (17.8 g), obtained as in Example 2 of Patent Document 1, was added with ethanol:water=1:2 (1000 mL) and heated and stirred until fully dissolved. The mixture was left to cool down to room temperature, the precipitated crystal was filtered and washed with ethanol:water=1:5, and then dried at 40° C. under reduced pressure to obtain the α-form crystal (16.5 g) mentioned above.

FIG. 7 shows the differential scanning calorimeter analysis curve (DSC analysis curve) of the α-form crystal, and FIG. 8 shows the X-ray powder diffraction pattern of the α-form crystal.

Comparative Example

δ-form Crystal of 4-[3-isopropyl-5-(6-phenyl-3-pyridyl)-4H-1,2,4-triazol-4-yl]-2,1,3-benzoxadiazole Example 2 of the Patent Document 1 was additionally carried out to obtain the δ-form crystal mentioned above. Furthermore, 150 mg of the β-form crystal of 4-[3-isopropyl-5-(6-phenyl-3-pyridyl)-4H-1,2,4-triazol-4-yl]-2,1,3-benzoxadiazole was added with 5 mL of cyclohexane/methylethyl ketone mixture (7:3) and heated until fully dissolved, added with 15 mL of cyclohexane and ice-cooled, and then the crystal was collected by filtration to obtain the δ-form crystal of 4-[3-isopropyl-5-(6-phenyl-3-pyridyl)-4H-1,2,4-triazol-4-yl]-2,1,3-benzoxadiazole.

FIG. 5 shows the differential scanning calorimeter analysis curve (DSC analysis curve) of the δ-form crystal, and FIG. 6 shows the X-ray powder diffraction pattern of the δ-form crystal.

Industrial Applicability

The crystals of the present invention hardly exhibit hygroscopicity, and particularly have excellent photo-resistance thereby being excellent in preservation stability, and are also useful as an inhibitor of glycine transporter activity, for example, as a therapeutic agent for dementia, schizophrenia, or cognitive disorders associated with various diseases such as Alzheimer's disease, Parkinson's disease or Huntington's disease, or contractures associated with diseases such as neurodegenerative diseases or cerebrovascular disorders.

It was confirmed from the hygroscopicity test mentioned below that the β-form crystal and the γ-form crystal of the present invention exhibit no hygroscopicity, and that the α-form crystal has an excellent property of exhibiting relatively low hygroscopicity as compared to the known δ-form crystal.

(Hygroscopicity Test)

For the measurement of hygroscopicity, "VTI SGA-100" was used under the conditions of temperature: 25° C., measurement range: 5 to 95% relative humidity, and measurement interval: 5% relative humidity.

The hygroscopicity curves of the β-form crystal, the γ-form crystal and the α-form crystal of the present invention are shown in FIG. 9, FIG. 10 and FIG. 12, respectively. In addition, the hygroscopicity curve diagram of the known δ-form crystal is shown in FIG. 11.

perature: 25° C.) of integrated luminance, using a light stability testing device LTL-200D3J-15.

HPLC Conditions

Device: LC1100 (LC-5) manufactured by Agilent

Mobile phase: A: 0.01 mol/L, $NaClO_4$ buffer (pH 2.5), B: MeCN

Flow rate: 0.2 mL/min

Column: Inertsil ODS-3 3 um (2.1 mm×100 mm)

Column temperature: 40° C.

Gradient condition: Bconc. 20 to 90% (0 to 18 min), 90% (18 to 23 min), 20% (23.1 to 33 min)

Injection volume: 1 μL

Autosampler temperature: 5° C.

Detection wavelength: 254 nm

The increased amount of impurity in the β-form crystal, the γ-form crystal and the α-form crystal of the present invention, and the known δ-form crystal, after preservation of the crystals, is shown in Table 2.

TABLE 2

|  | β-form Crystal (crystal of present invention) | γ-form Crystal (crystal of present invention) | α-form Crystal (crystal of present invention) | δ-form Crystal (known crystal) |
| --- | --- | --- | --- | --- |
| Impurity Increase Amount (%) | 0.0 | 0.0 | 0.0 | 1.0 |

As is clear from FIG. 11, the known δ-form crystal started exhibiting hygroscopicity gradually from a relative humidity of about 50%, showed a drastic increase in weight from a relative humidity of about 80%, and showed to retain approximately 2% of moisture at a relative humidity of about 95%.

On the other hand, the β-form crystal and the γ-form crystal of the present invention showed almost no change in weight from low humidity to high humidity, and were found to hardly exhibit hygroscopicity (see FIG. 9 and FIG. 10: throughout the whole range from 5% relative humidity to 95% relative humidity, the moisture retaining amount for each crystal was 0.2% or less).

In addition, although the α-form crystal of the present invention did exhibit certain hygroscopicity, the hygroscopicity was found to be less than that of the known δ-form crystal (see FIG. 12).

In Japan, the humidity often exceeds 50%, and thus it is extremely inappropriate to employ crystals exhibiting hygroscopicity as drug substances for pharmaceutical agents. Firstly, it is extremely difficult to obtain bulk drugs which do not include any moisture or uniform bulk drugs which include consistently restricted amount of moisture in performing mass synthesis of bulk drugs for pharmaceutical agents. Secondly, the physical and chemical qualities or properties such as stability of the crystals may change depending on the state of retained moisture. Thirdly, numerous limitations can occur due to the necessity of incorporating special drug manufacturing processes, since hygroscopicity can be exhibited in the processes of storage, transportation or drug manufacturing of the crystals. Fourthly, even after manufacture, the drugs may easily exhibit hygroscopicity, resulting in poor stability.

The excellent photo-resistance of the β-form crystal, the γ-form crystal and the α-form crystal of the present invention have been verified by the photo stability test below.

(Photo Stability Test)

The amount of impurity was measured through HPLC using a preserved sample, under 1.2 million lux-hours (tem- The photo stability at 1.2 million lux-hours of integrated luminance is designated as the ICH guideline for photo stability testing, and thus is an important guideline for identification of photodegradable materials, confirmation of safety and determination for the necessity of photo-shielding protection. In the known δ-form crystal, a 1.0% increase in impurities after preservation was observed, whereas in the β-form crystal, the γ-form crystal and the α-form crystal of the present invention, the increase in impurity were 0.0%. Considering that the threshold for impurities with special conditions (structure determined, and safety confirmed) is 0.1% in the ICH guideline, 1.0% is a very high value, and therefore photo-shielding preservation is a necessity for the known δ-form crystal. On the other hand, photo-shielding is unnecessary for the β-form crystal, the γ-form crystal and the α-form crystal of the present invention, so not only is their convenience as pharmaceutical products improved, but there is also a huge advantage in that there is no need to incorporate special drug manufacturing processes such as manufacture under a photo-shield.

The excellent glycine transporter inhibition effect of the β-form crystal, the γ-form crystal and the α-form crystal of the present invention have been verified by the pharmacological test below.

(Pharmacological Test)

Confirmation Test for Glycine Transporter (GLYT) Activation Inhibition Effect

1) Cell Culture

Rat C6 glioma cells that express a subtype of glycine transporter, GLYT1 (see J. Gomeza, F. Zafra, L. Olivares, C. Gimenez, C. Aragon, Regulation by phorbol esters of the glycine transporter (GLYT1) in glioblastoma cells., Biochim. Biophys. Acta., 1233, 41-46, 1995) were used.

The C6 glioma cells (American Type Culture Collection) were cultured in a $CO_2$ incubator under the conditions of 5% $CO_2$, and 37° C. in a DMEM (Dulbecco's Modified Eagles's Medium) including 10% fetal calf serum, 100 units/ml penicillin G and 0.1 mg/ml streptomycin sulfate.

2) [$^3$H] Glycine Uptake

[$^3$H] glycine uptake was carried out according to the method of Gomeza et al. (J. Gomeza, F. Zafra, L. Olivares, C. Gimenez, C. Aragon, Biochim. Biophys. Acta., 1233, 41-46, 1995).

The C6 glioma cells were seeded in 96 well plates (Culturplate, manufactured by PerkinElmer) in a concentration of 2×10$^4$ cells/well, cultured for 2 days, and then the experiment on the [$^3$H] glycine uptake was carried out. The cells were washed once with a buffer (150 mM NaCl, 5 mM KCl, 1 mM CaCl$_2$, 1 mM MgCl$_2$, 10 mM glucose, 5 mM L-alanine and 10 mM Hepes-Na, pH 7.4), added with the buffer once more, and then incubated at 37° C. for 10 minutes.

After the incubation, the buffer was exchanged with a reaction buffer including [$^3$H] glycine (approximately 0.14 μM, 50 to 60 Ci/mmol, manufactured by PerkinElmer) and the evaluation compound, and then incubated at 37° C. for another 20 minutes. After the 20-minute reaction, it was washed with ice-cooled PBS (phosphate buffered saline). The cells were lysed with 0.1 N NaOH solution, and the uptake of the radioactivity amount was measured with a liquid scintillation counter. The specific uptake was defined as the portion substituted by 3 mM sarcosine among the whole uptake. The evaluation of the test compound was carried out by calculating the uptake inhibition rate for the specific uptake.

As a result, the β-form crystal, the γ-form crystal and the α-form crystal of the present invention showed high inhibition effect against the [$^3$H] glycine uptake which was equal to the value (0.10 μM) shown in Example 2 of Table 1 in Patent Document 1.

Figure 1:
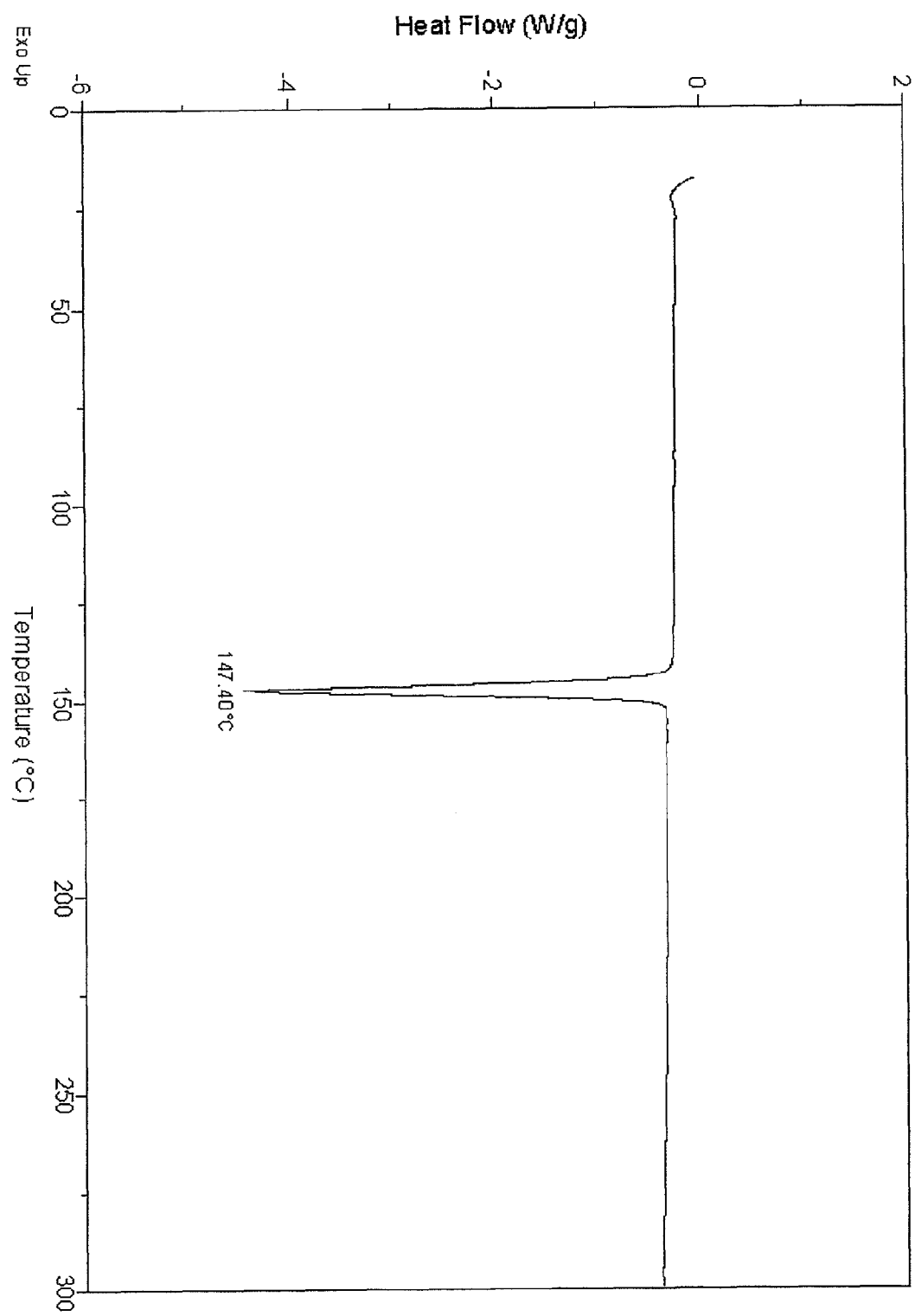
FIG. 1 is a differential scanning calorimeter analysis curve (DSC analysis curve) of β-form crystal (crystal of the present invention) of 4-[3-isopropyl-5-(6-phenyl-3-pyridyl)-4H-1,2,4-triazol-4-yl]-2,1,3-benzoxadiazole.
Figure 2:
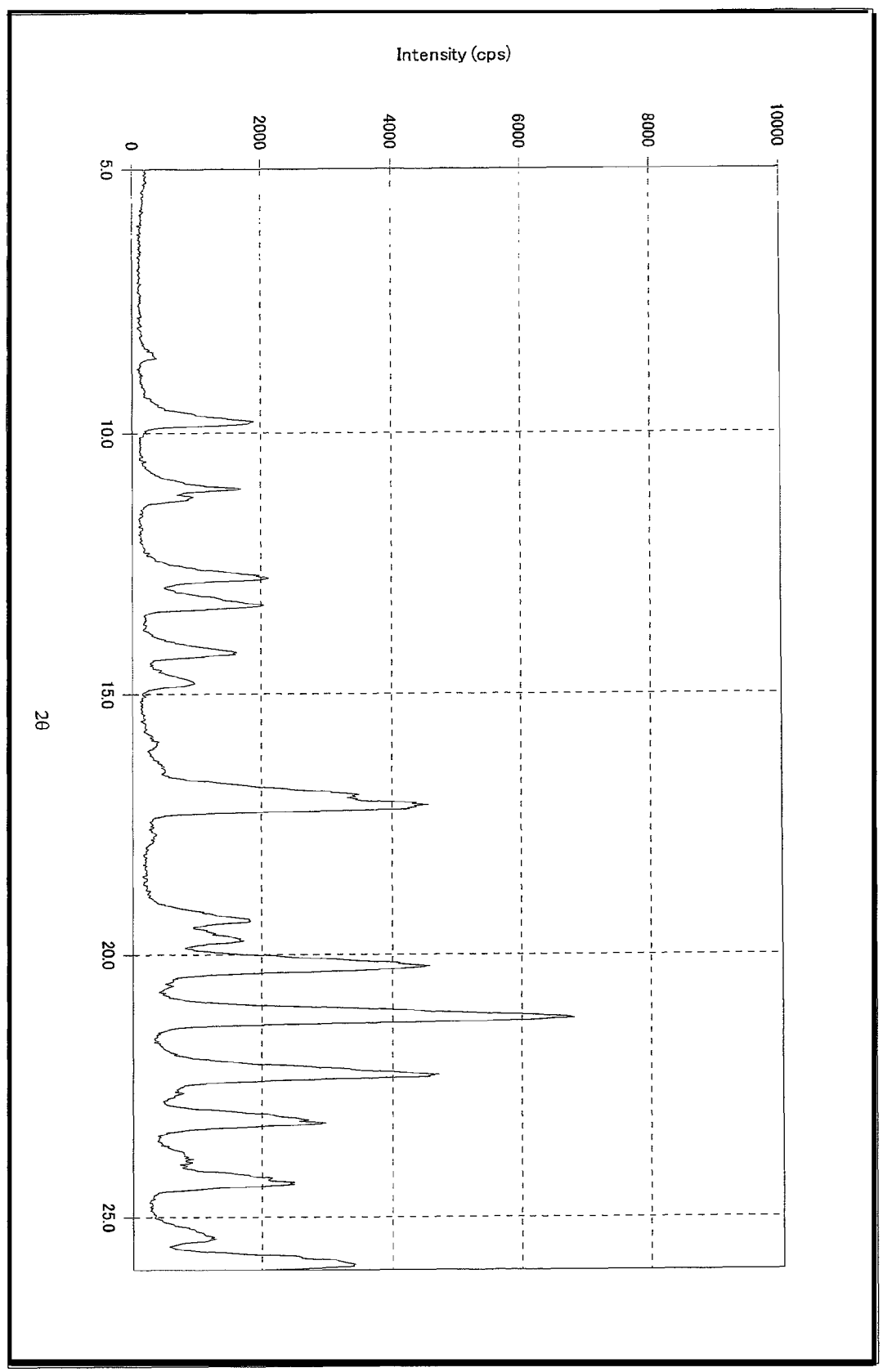
FIG. 2 is an X-ray powder diffraction pattern of the β-form crystal (the crystal of the present invention) of 4-[3-isopropyl-5-(6-phenyl-3-pyridyl)-4H-1,2,4-triazol-4-yl]-2,1,3-benzoxadiazole.
Figure 3:
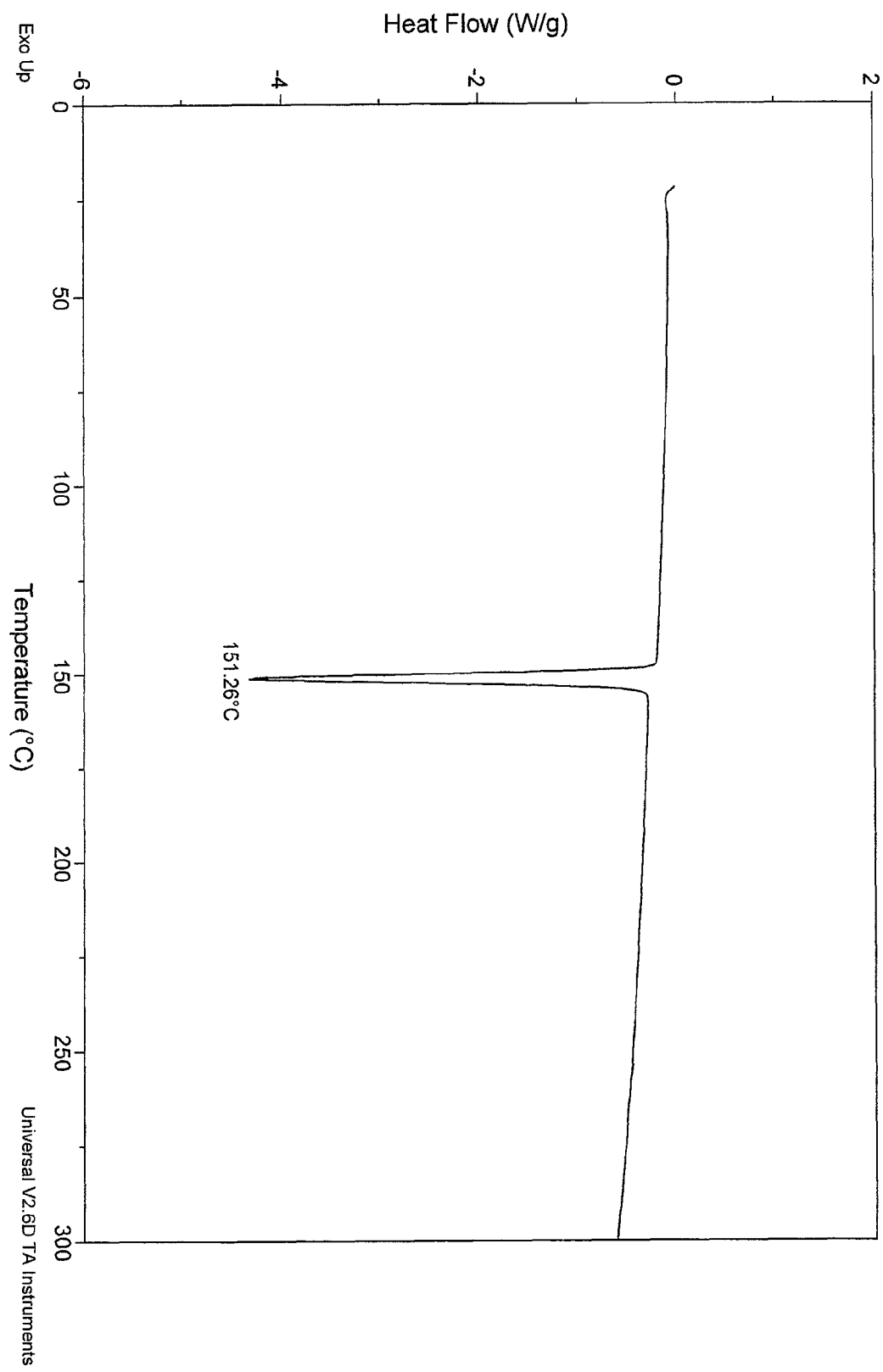
FIG. 3 is a differential scanning calorimeter analysis curve (DSC analysis curve) of γ-form crystal (crystal of the present invention) of 4-[3-isopropyl-5-(6-phenyl-3-pyridyl)-4H-1,2,4-triazol-4-yl]-2,1,3-benzoxadiazole.
Figure 4:
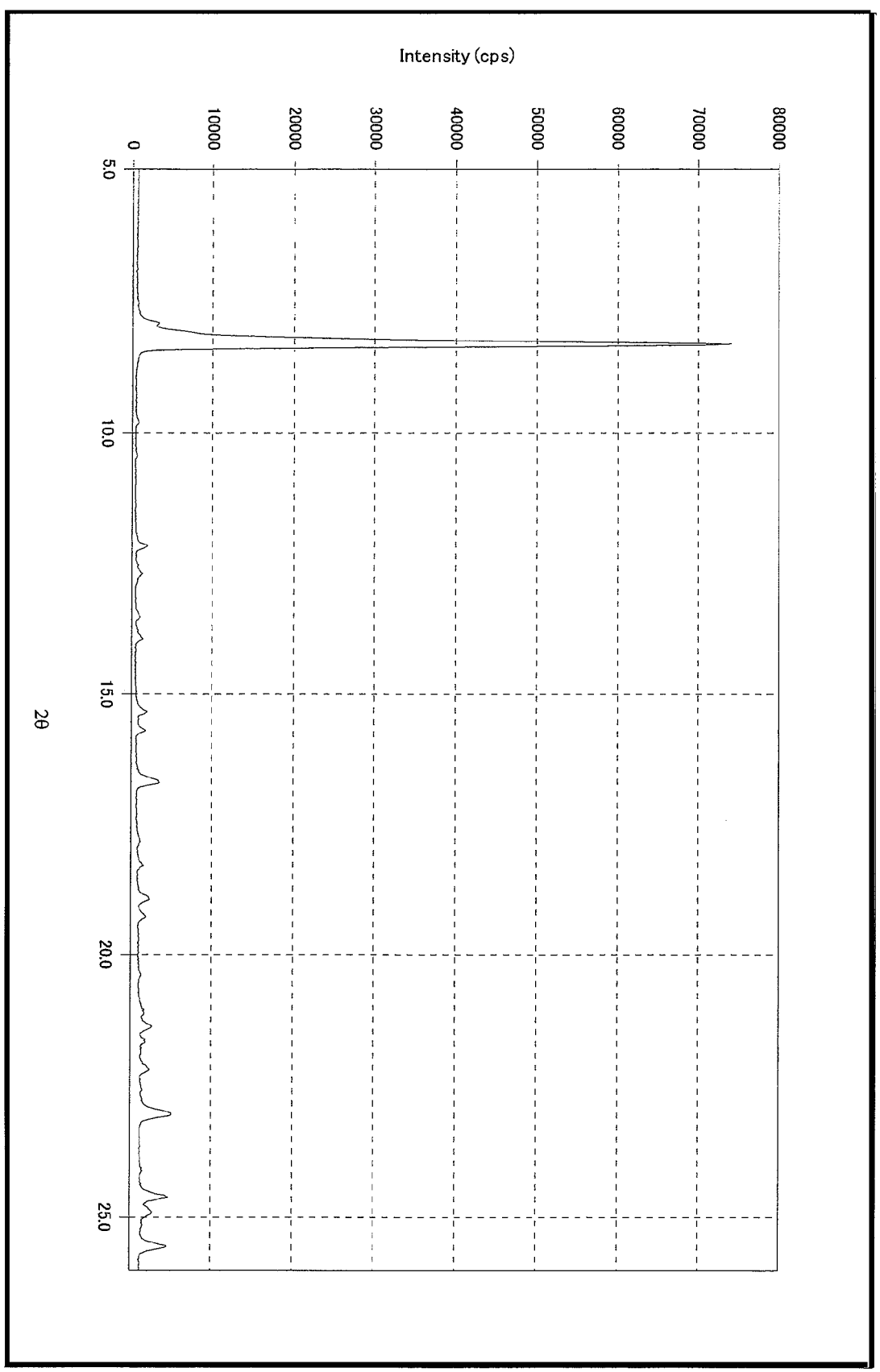
FIG. 4 is an X-ray powder diffraction pattern of the γ-form crystal (the crystal of the present invention) of 4-[3-isopropyl-5-(6-phenyl-3-pyridyl)-4H-1,2,4-triazol-4-yl]-2,1,3-benzoxadiazole.
Figure 5:
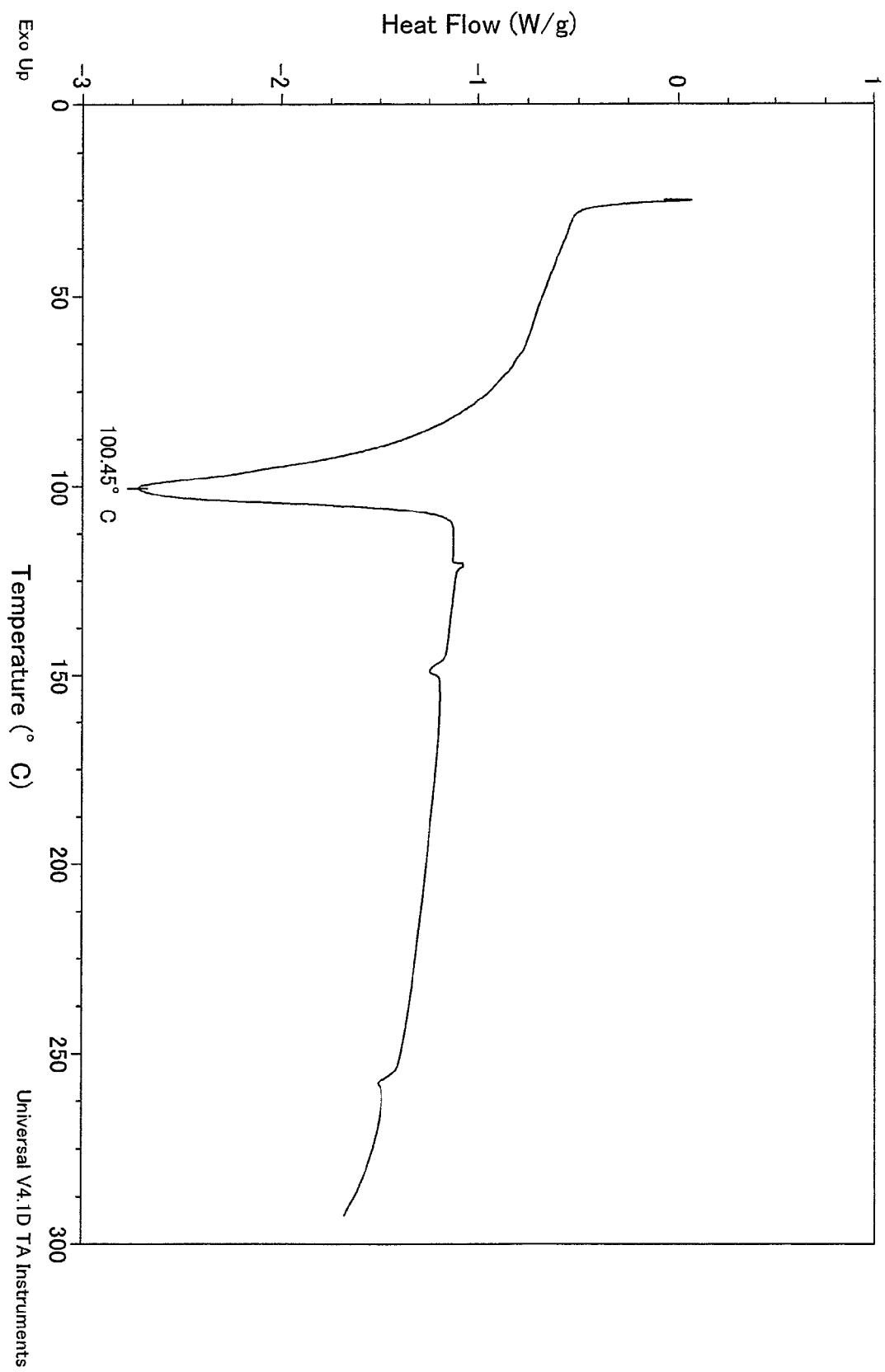
FIG. 5 is a differential scanning calorimeter analysis curve (DSC analysis curve) of the δ-form crystal (the known crystal) of 4-[3-isopropyl-5-(6-phenyl-3-pyridyl)-4H-1,2,4-triazol-4-yl]-2,1,3-benzoxadiazole.
Figure 6:
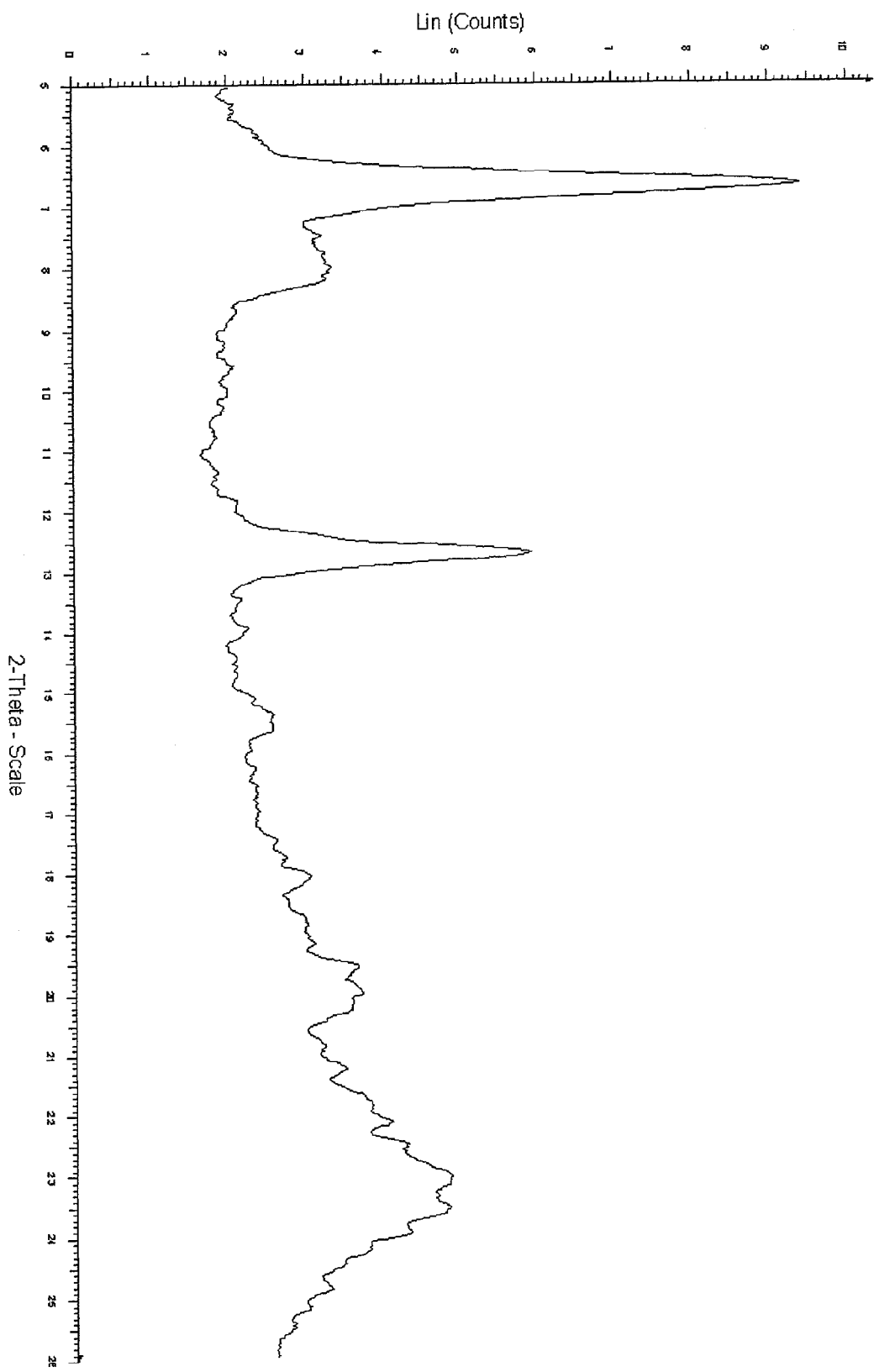
FIG. 6 is an X-ray powder diffraction pattern of the δ-form crystal (the known crystal) of 4-[3-isopropyl-5-(6-phenyl-3-pyridyl)-4H-1,2,4-triazol-4-yl]-2,1,3-benzoxadiazole.
Figure 7:
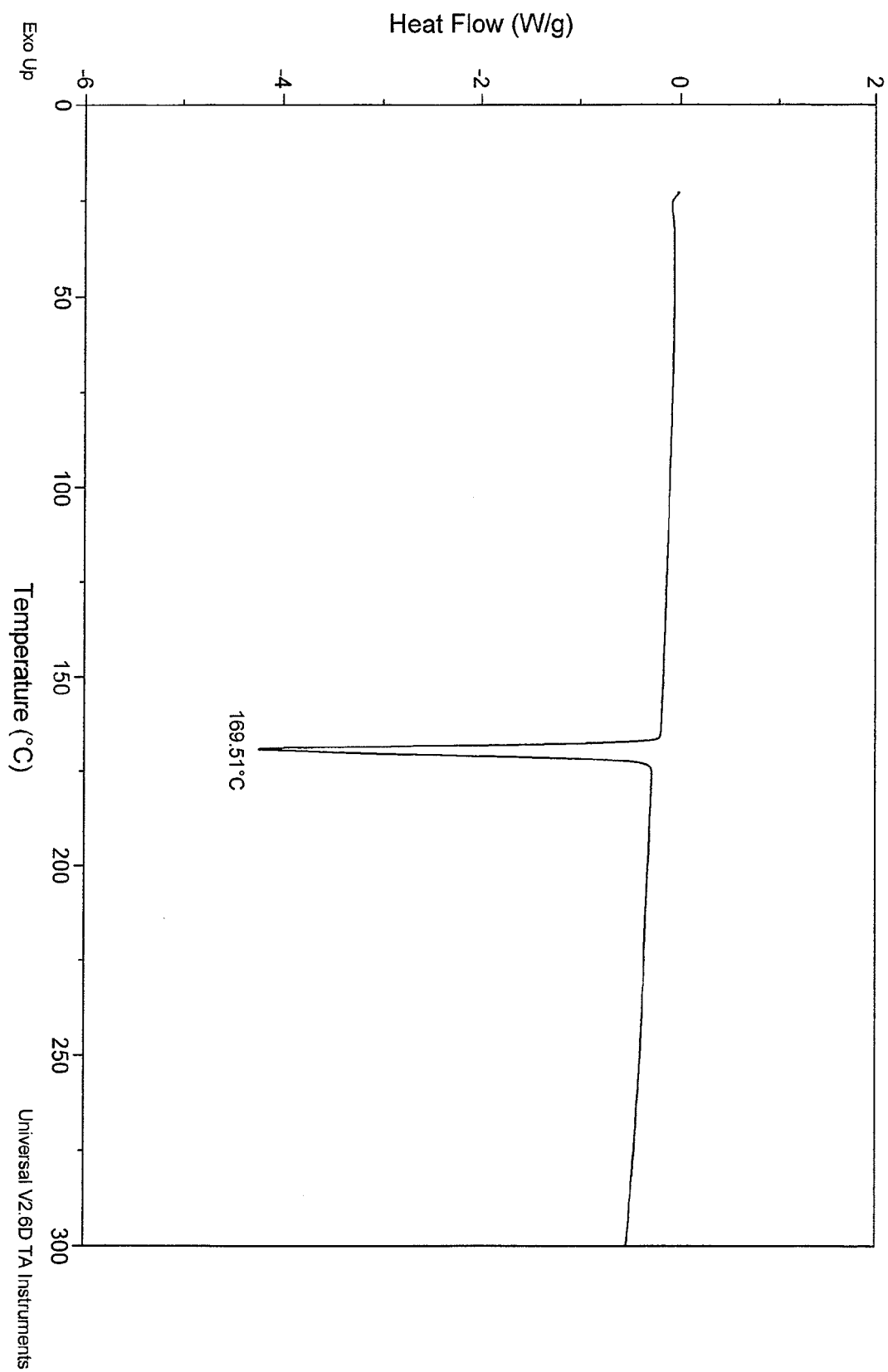
FIG. 7 is a differential scanning calorimeter analysis curve (DSC analysis curve) of α-form crystal (crystal of the present invention) of 4-[3-isopropyl-5-(6-phenyl-3-pyridyl)-4H-1,2,4-triazol-4-yl]-2,1,3-benzoxadiazole.
Figure 8:
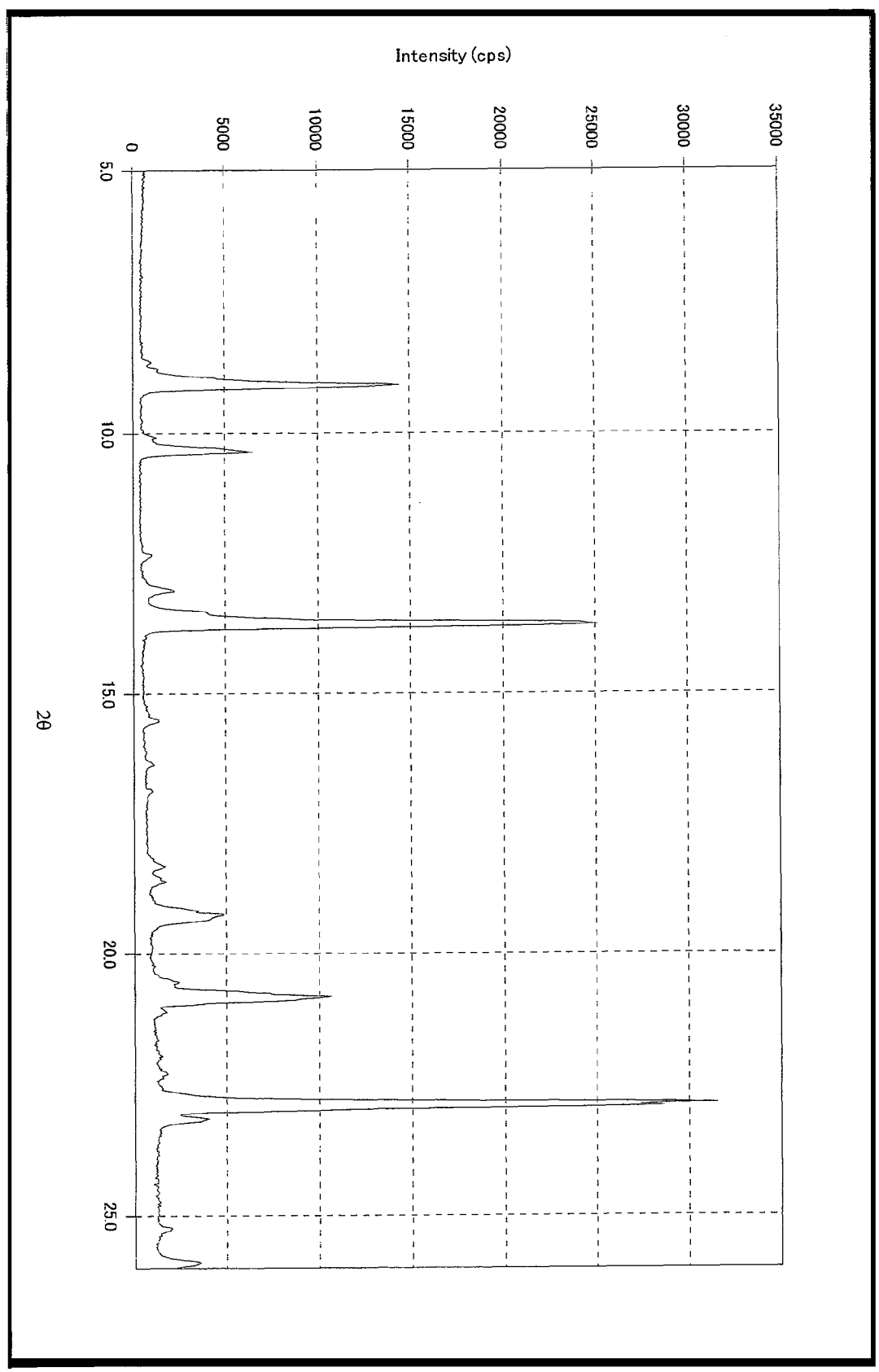
FIG. 8 is an X-ray powder diffraction pattern of the α-form crystal (the crystal of the present invention) of 4-[3-isopropyl-5-(6-phenyl-3-pyridyl)-4H-1,2,4-triazol-4-yl]-2,1,3-benzoxadiazole.
Figure 9:
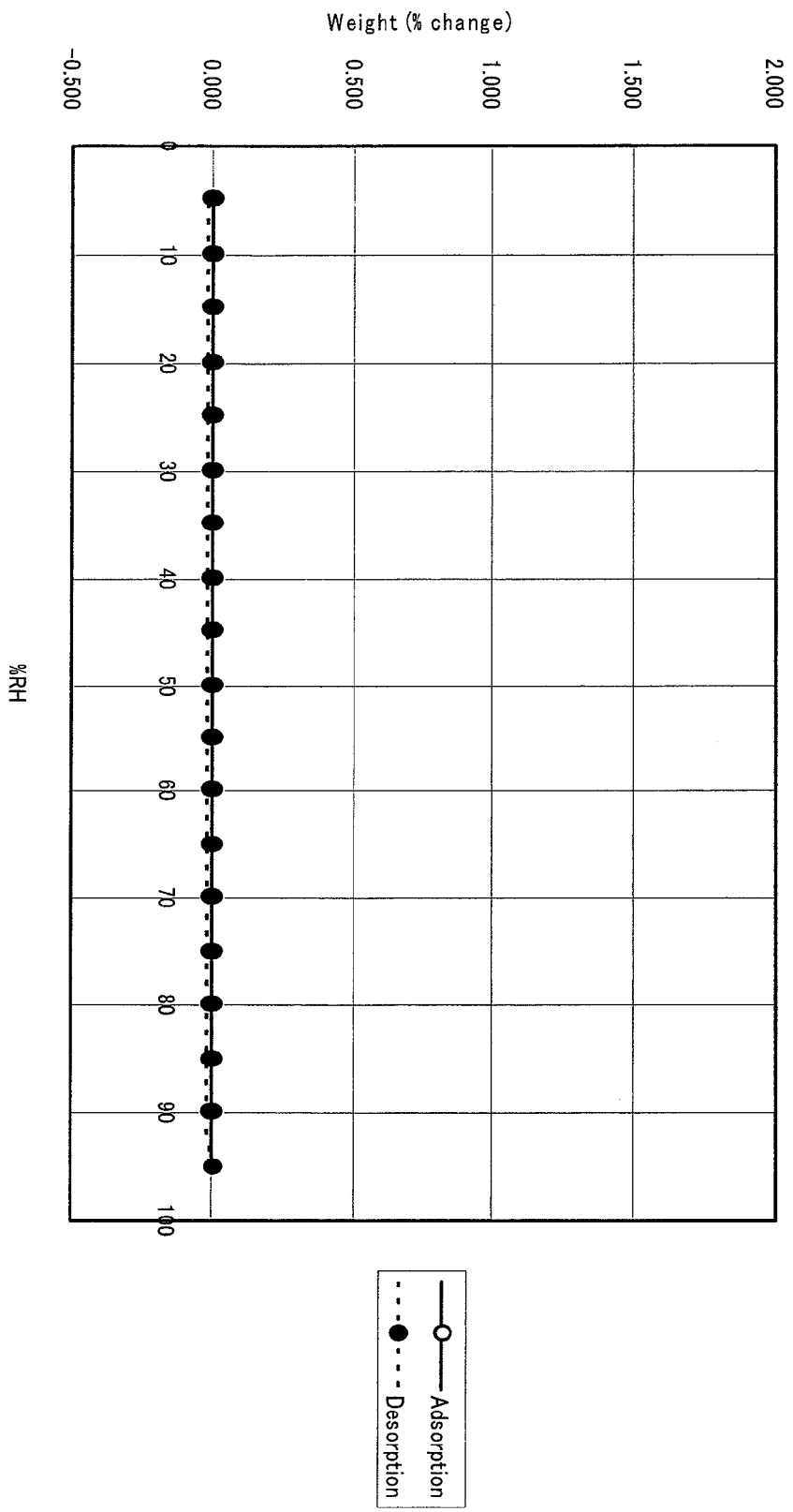
FIG. 9 is a hygroscopicity curve of β-form crystal (crystal of the present invention) of 4-[3-isopropyl-5-(6-phenyl-3-pyridyl)-4H-1,2,4-triazol-4-yl]-2,1,3-benzoxadiazole.
Figure 10:
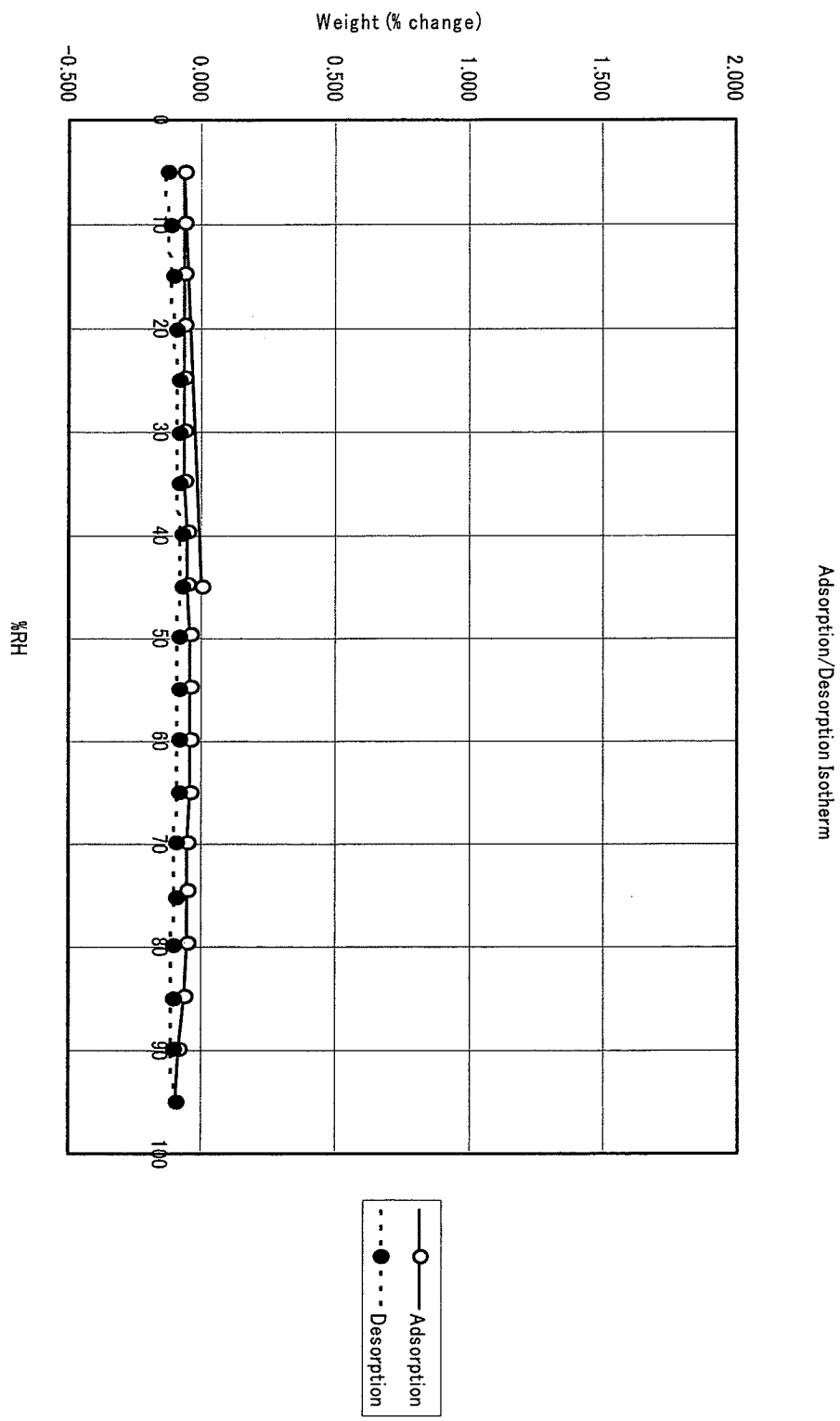
FIG. 10 is a hygroscopicity curve of the γ-form crystal (the crystal of the present invention) of 4-[3-isopropyl-5-(6-phenyl-3-pyridyl)-4H-1,2,4-triazol-4-yl]-2,1,3-benzoxadiazole.
Figure 11:
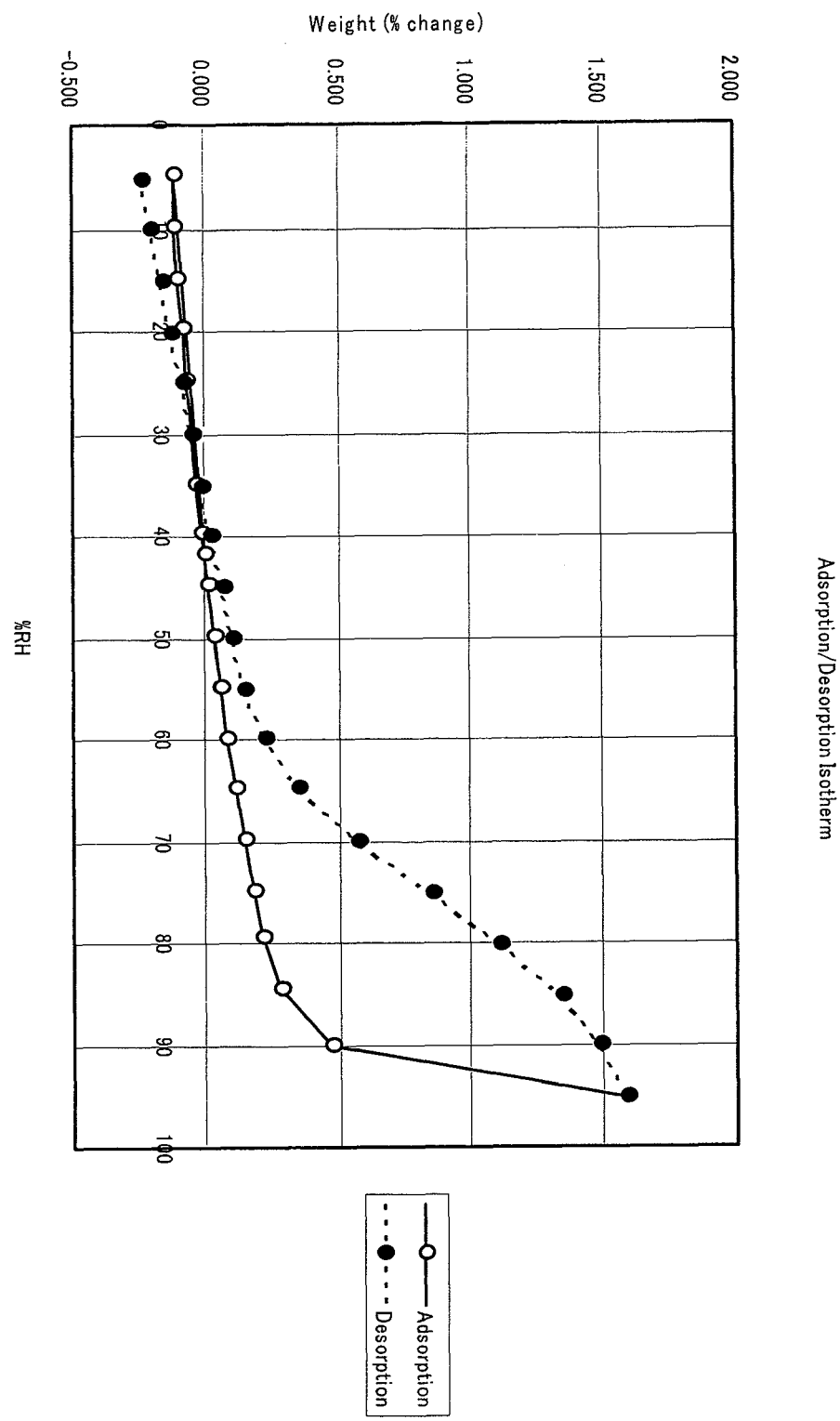
FIG. 11 is a hygroscopicity curve of the δ-form crystal (the known crystal) of 4-[3-isopropyl-5-(6-phenyl-3-pyridyl)-4H-1,2,4-triazol-4-yl]-2,1,3-benzoxadiazole.
Figure 12:
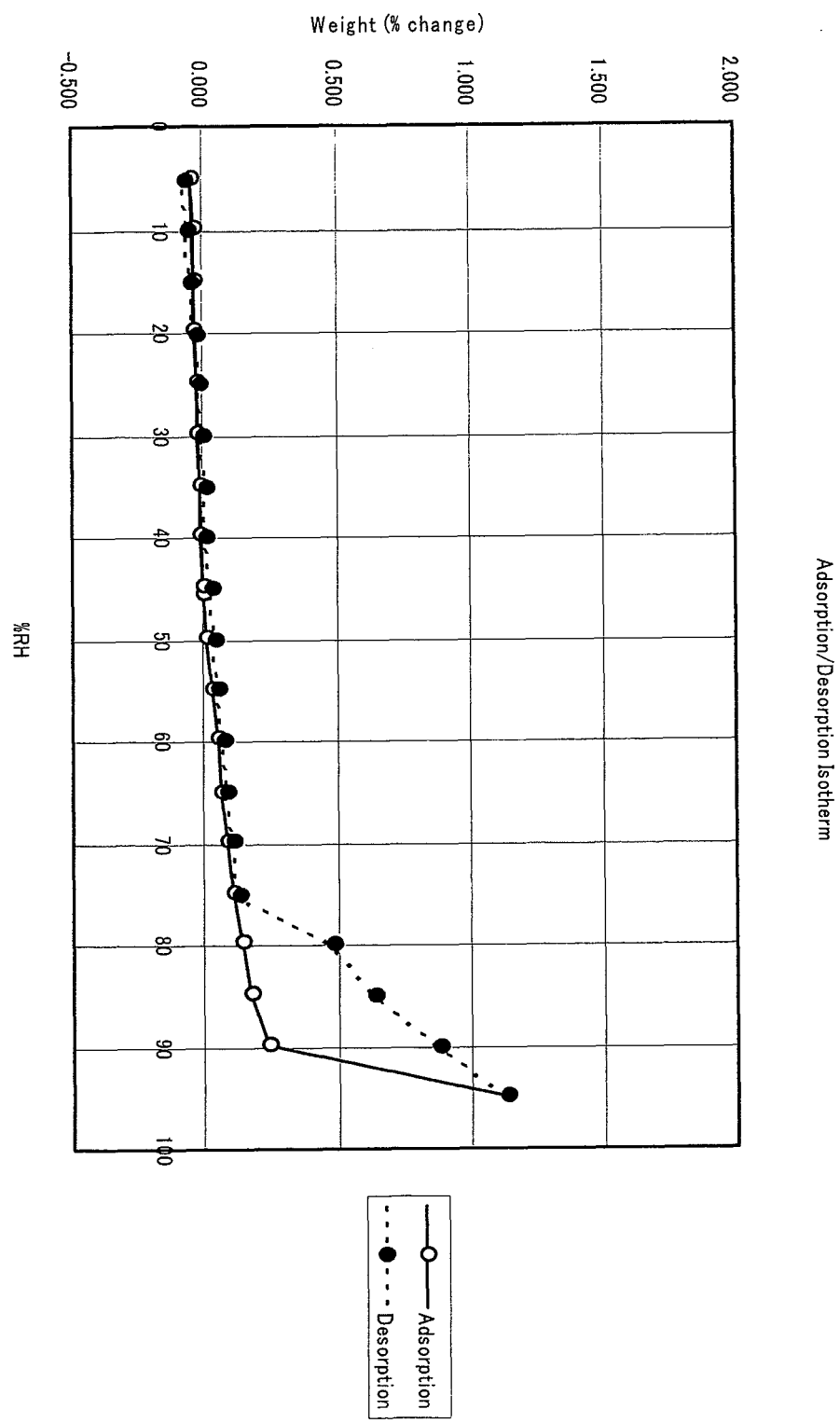
FIG. 12 is a hygroscopicity curve of the α-form crystal (the crystal of the present invention) of 4-[3-isopropyl-5-(6-phenyl-3-pyridyl)-4H-1,2,4-triazol-4-yl]-2,1,3-benzoxadiazole.

The invention claimed is:

1. A β-form crystal of 4-[3-isopropyl-5-(6-phenyl-3-pyridyl)-4H-1,2,4-triazol-4-yl]-2,1,3-benzoxadiazole, which shows an endothermic peak at 145 to 150° C. according to a differential scanning calorimeter analysis (DSC analysis).

2. A β-form crystal of 4-[3-isopropyl-5-(6-phenyl-3-pyridyl)-4H-1,2,4-triazol-4-yl]-2,1,3-benzoxadiazole, which shows X-ray powder diffraction peaks at 9.8, 11.1, 12.8, 13.3, 17.1, 20.2, 21.2 and 22.3 in 2θ(°).

3. A β-form crystal of 4-[3-isopropyl-5-(6-phenyl-3-pyridyl)-4H-1,2,4-triazol-4-yl]-2,1,3-benzoxadiazole, which shows an endothermic peak at 145 to 150° C. according to a differential scanning calorimeter analysis (DSC analysis) and shows X-ray powder diffraction peaks at 9.8, 11.1, 12.8, 13.3, 17.1, 20.2, 21.2 and 22.3 in 2θ(°).

4. A pharmaceutical composition comprising crystals of the β-form crystal according to any one of claims 1, 2 and 3 as an active ingredient and a pharmaceutically acceptable excipient.

\* \* \* \* \*